(12) United States Patent
Saji et al.

(10) Patent No.: US 10,080,812 B2
(45) Date of Patent: Sep. 25, 2018

(54) RADIOACTIVE IODINE LABELED PYRIDO[1,2-A]BENZOIMIDAZOLE DERIVATIVE COMPOUND

(71) Applicants: KYOTO UNIVERSITY, Kyoto-shi, Kyoto (JP); NIHON MEDI-PHYSICS CO., LTD., Koto-ku, Tokyo (JP)

(72) Inventors: Hideo Saji, Kyoto (JP); Masahiro Ono, Kyoto (JP); Masafumi Ihara, Kyoto (JP); Ikuya Seki, Tokyo (JP)

(73) Assignees: KYOTO UNIVERSITY, Kyoto-Shi, Kyoto (JP); NIHON MEDI-PHYSICS CO., LTD., Kyoto-Ku, Tokyo (JP)

( * ) Notice: Subject to any disclaimer, the term of this patent is extended or adjusted under 35 U.S.C. 154(b) by 0 days.

(21) Appl. No.: 15/543,857

(22) PCT Filed: Feb. 24, 2016

(86) PCT No.: PCT/JP2016/055356
§ 371 (c)(1),
(2) Date: Jul. 14, 2017

(87) PCT Pub. No.: WO2016/140118
PCT Pub. Date: Sep. 9, 2016

(65) Prior Publication Data
US 2018/0000974 A1 Jan. 4, 2018

(30) Foreign Application Priority Data
Mar. 4, 2015 (JP) ................................. 2015-042748

(51) Int. Cl.
| | | |
|---|---|---|
| C07B 59/00 | (2006.01) | |
| C07B 63/04 | (2006.01) | |
| C07D 471/04 | (2006.01) | |
| A61K 51/04 | (2006.01) | |
| C07F 7/22 | (2006.01) | |

(52) U.S. Cl.
CPC .......... *A61K 51/0455* (2013.01); *C07B 59/00* (2013.01); *C07D 471/04* (2013.01); *C07F 7/2212* (2013.01); *C07B 2200/05* (2013.01)

(58) Field of Classification Search
CPC .. A61K 51/0455; C07B 59/00; C07D 471/04; C07F 7/2212
USPC .......................................................... 546/84
See application file for complete search history.

(56) References Cited

U.S. PATENT DOCUMENTS

| | | |
|---|---|---|
| 2010/0239496 A1 | 9/2010 | Gangadharmath et al. |
| 2011/0182812 A1 | 7/2011 | Szardenings et al. |
| 2012/0302755 A1 | 11/2012 | Szardenings et al. |
| 2012/0330024 A1 | 12/2012 | Saji et al. |

FOREIGN PATENT DOCUMENTS

| | | |
|---|---|---|
| JP | 2012-521988 A | 9/2012 |
| JP | 2013-522365 A | 6/2013 |
| JP | 2013-237655 A | 11/2013 |
| JP | 2015-089879 A | 5/2015 |
| JP | 2015-517572 A | 6/2015 |
| WO | WO 2011/108236 A1 | 9/2011 |
| WO | WO 2013/176698 A1 | 11/2013 |

OTHER PUBLICATIONS

International Search Report (PCT/ISA/210) dated Apr. 19, 2016, by the Japanese Patent Office as the International Searching Authority for International Application No. PCT/JP2016/055357.
Written Opinion (PCT/ISA/237) dated Apr. 19, 2016, by the Japanese Patent Office as the International Searching Authority for International Application No. PCT/JP2016/055357.
International Search Report (PCT/ISA/210) dated Apr. 19, 2016, by the Japanese Patent Office as the International Searching Authority for International Application No. PCT/JP2016/055356.
Written Opinion (PCT/ISA/237) dated Apr. 19, 2016, by the Japanese Patent Office as the International Searching Authority for International Application No. PCT/JP2016/055356.
"DVD Abstracts of the 135 Annual Meeting of the Pharmaceutical Society of Japan in Kobe" Mar. 5, 2015, with Certificates for receiving the application of the provisions of the exception of the novelty of the loss of the invention 1. (7 pages).

*Primary Examiner* — Rita J Desai
(74) *Attorney, Agent, or Firm* — Buchanan, Ingersoll & Rooney PC

(57) ABSTRACT

The present invention relates to a radioactive iodine-labeled pyrido[1,2-a]benzimidazole derivative compound represented by a definite general formula or a salt thereof, or a radiopharmaceutical comprising the same.

8 Claims, 6 Drawing Sheets

RADIOACTIVE IODINE LABELED PYRIDO[1,2-A]BENZOIMIDAZOLE DERIVATIVE COMPOUND

TECHNICAL FIELD

The present invention relates to a radioactive iodine-labeled pyrido[1,2-a]benzimidazole derivative compound or a salt thereof, and a radiopharmaceutical comprising the same.

RELATED ART

Accumulation of senile plaque (SP) composed mainly of amyloid β protein (Aβ) and neurofibrillary tangle (NFT) composed mainly of tau protein is found in the brain with Alzheimer's disease (AD). Since the accumulation of NFT exhibits high correlation with clinical symptoms, as compared with SP, development of radioactive molecule imaging probes for nuclear medicine diagnosis targeting the tau protein has received attention recently.

For example, Patent Document 1 describes radioactive iodine-labeled compounds comprising rhodanine and thiohydantoin derivatives having affinity for the tau protein.

Also, Patent Documents 2 and 3 describe compounds having binding activity against both of the Aβ and the tau protein. Specifically, Patent Document 2 describes a radioactive iodine-labeled compound having styrylbenzimidazole as a nucleus, and Patent Document 3 describes benzimidazolepyrimidines and the like.

RELATED DOCUMENTS

Patent Documents

Patent Document 1: International Publication No. WO 2011/108236
Patent Document 2: Japanese Patent Laid-Open (Kokai) No. 2013-237655
Patent Document 3: Japanese Patent Laid-Open (Kohyo) No. 2013-522365

SUMMARY

However, the compounds described in Patent Documents 1 to 3 still need to be improved for in vivo imaging agents selective for the tau protein.

The present invention has been made in light of these circumstances, and aims to provide a novel tau imaging agent capable of selectively imaging a tau protein in living body by a nuclear medicine approach noninvasively.

The present inventors have completed the present invention by newly finding that a radioactive iodine-labeled pyrido[1,2-a]benzimidazole derivative compound suppresses the nonspecific accumulation to the white matter while maintaining selective binding activity against the tau protein.

One aspect of the present invention provides a radioactive iodine-labeled compound represented by the following general formula (1) or a salt thereof:

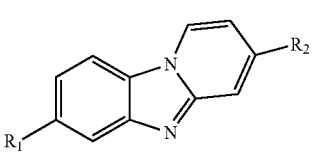

(1)

In the general formula (1), when $R_1$ is a hydrogen atom, $R_2$ is a radioactive iodine atom or a radioactive iodophenyl group, and when $R_1$ is a radioactive iodine atom, $R_2$ is a hydrogen atom or a phenyl group.

Another aspect of the present invention provides a radiopharmaceutical comprising the aforementioned radioactive iodine-labeled compound or a salt thereof.

Still another aspect of the present invention provides a diagnostic agent for Alzheimer's disease comprising the aforementioned radioactive iodine-labeled compound or a salt thereof.

Still another aspect of the present invention provides a compound represented by the following general formula (2) or a salt thereof:

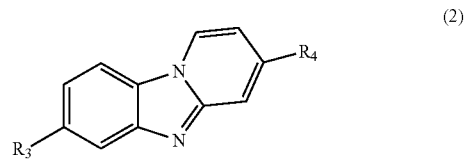

(2)

In the general formula (2), when $R_3$ is a hydrogen atom, $R_4$ is a trialkylstannyl group, a trialkylsilyl group, a trialkylstannyl phenyl group, or a trialkylsilyl phenyl group, and when $R_3$ is a trialkylstannyl group or a trialkylsilyl group, $R_4$ is a hydrogen atom or a phenyl group.

Still another aspect of the present invention provides a method for producing a radioactive iodine-labeled compound represented by the general formula (1) or a salt thereof from a compound represented by the general formula (2) or a salt thereof by radioactive iodination reaction.

The present invention can provide a novel tau imaging agent which is capable of selectively imaging a tau protein in living body by a nuclear medicine approach.

The object mentioned above and other objects, features, and advantages will become further apparent from the following preferred embodiments and the accompanying drawings shown below.

BRIEF DESCRIPTION OF DRAWINGS

FIG. 5A is a diagram showing a synthesis example of 7-[$^{125}$I]iodo-3-phenylbenzo[4,5]imidazo[1,2-a]pyridine ([$^{125}$I]BIP-1). FIG. 5B is a diagram showing a synthesis example of 3-(4-[$^{125}$I]iodophenyl)benzo[4,5]imidazo[1,2-a]pyridine ([$^{125}$I]BIP-2). FIG. 5C is a diagram showing a synthesis example of 7-[$^{125}$I]iodobenzo[4,5]imidazo[1,2-a]pyridine ([$^{125}$I]BIP-3). FIG. 5D is a diagram showing a synthesis example of 3-[$^{125}$I]iodobenzo[4,5]imidazo[1,2-a]pyridine ([$^{125}$I]BIP-4).

FIG. 6E shows results of evaluating the binding affinity of the radioactive iodine-labeled BIP-1 using a brain tissue section of the temporal lobe. FIG. 6F shows results of evaluating the binding affinity of [$^{125}$I]BIP-1 using a brain tissue section of the frontal lobe. FIG. 6G shows results of evaluating the binding affinity of [$^{125}$I]BIP-2 using a brain tissue section of the temporal lobe. FIG. 6H shows results of evaluating the binding affinity of [$^{125}$I]BIP-2 using a brain tissue section of the frontal lobe. FIG. 6I shows results of evaluating the binding affinity of [$^{125}$I]BIP-3 using a brain tissue section of the temporal lobe. FIG. 6J shows results of evaluating the binding affinity of [$^{125}$I]BIP-3 using a brain tissue section of the frontal lobe. FIG. 6K shows results of evaluating the binding affinity of [$^{125}$I]BIP-4 using a brain tissue section of the temporal lobe. FIG. 6L shows results of evaluating the binding affinity of [$^{125}$I]BIP-4 using a brain tissue section of the frontal lobe.

FIG. 7M shows results of immunostaining with an antibody against tau. FIG. 7O shows results of immunostaining with an antibody against Aβ. FIG. 7N is an enlarged image of FIG. 6I.

DESCRIPTION OF EMBODIMENTS

Figure 1:
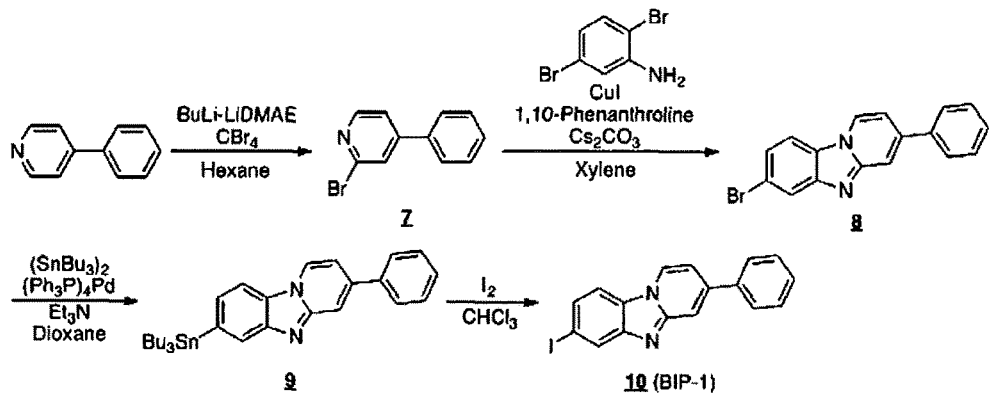
FIG. 1 is a diagram showing a synthesis example of 7-iodo-3-phenylbenzo[4,5]imidazo[1,2-a]pyridine (BIP-1) and a labeling precursor compound for the radioactive iodine-labeled BIP-1.

In the present invention, the "radioactive iodine" is not particularly limited as long as it is a radioisotope of iodine, but is preferably a radioactive species used in nuclear medicine diagnostic imaging such as single photon emission computed tomography (SPECT), more preferably, $^{123}$I, $^{124}$I, $^{125}$I, or $^{131}$I. $^{123}$I is furthermore preferred for nuclear medicine diagnostic imaging.

In the present invention, the "radioactive iodophenyl group" can be any substituent resulting from substitution of at least one hydrogen atom of the phenyl group with a radioactive iodine atom, and is preferably a monoiodophenyl group resulting from substitution of one hydrogen atom of the phenyl group with a radioactive iodine atom, more preferably a iodophenyl group resulting from substitution of a hydrogen atom at position 2, 3, or 4 of the phenyl group with a radioactive iodine atom, and furthermore preferably a substituent resulting from substitution of a hydrogen atom at position 4 of the phenyl group with a radioactive iodine atom (radioactive 4-iodophenyl group).

The radioactive iodine-labeled compound represented by the general formula (1) may form a salt. Examples of the salt include acid addition salts, for example, inorganic acid salts (e.g., hydrochloride, sulfate, hydrobromide, and phosphate) and organic acid salts (e.g., acetate, trifluoroacetate, succinate, maleate, fumarate, propionate, citrate, tartrate, lactate, oxalate, methanesulfonate, and p-toluenesulfonate). The compound represented by the general formula (1) or the salt thereof may be a hydrate.

Specific examples of the radioactive iodine-labeled compound according to the present invention include the following compounds:

radioactive iodine-labeled 7-iodo-3-phenylbenzo[4,5]imidazo[1,2-a]pyridine (a radioactive iodine-labeled compound of the general formula (1) wherein $R_1$ is a radioactive iodine atom, and $R_2$ is a phenyl group), radioactive iodine-labeled 3-(4-iodophenyl)benzo[4,5]imidazo[1,2-a]pyridine (a radioactive iodine-labeled compound of the general formula (1) wherein $R_1$ is a hydrogen atom, and $R_2$ is a radioactive 4-iodophenyl group), radioactive iodine-labeled 7-iodobenzo[4,5]imidazo[1,2-a]pyridine (a radioactive iodine-labeled compound of the general formula (1) wherein $R_1$ is a radioactive iodine atom, and $R_2$ is a hydrogen atom), and radioactive iodine-labeled 3-iodobenzo[4,5]imidazo[1,2-a]pyridine (a radioactive iodine-labeled compound of the general formula (1) wherein $R_1$ is a hydrogen atom, and $R_2$ is a radioactive iodine atom).

Subsequently, a method for producing the radioactive iodine-labeled compound represented by the general formula (1) or the salt thereof will be described. The radioactive iodine-labeled compound represented by the general formula (1) or the salt thereof can be obtained by carrying out a radioactive iodination reaction using a compound represented by the general formula (2) or a salt thereof.

The trialkylstannyl group in the general formula (2) includes tri(C1-C6 alkyl)stannyl groups, and more preferably a tributylstannyl group. The trialkylsilyl group includes tri(C1-C6 alkyl)silyl groups, and more preferably a trimethylsilyl group.

In the present invention, the "trialkylstannyl phenyl group" can be any substituent resulting from substitution of at least one hydrogen atom of the phenyl group with a trialkylstannyl group, and is preferably a substituted phenyl group resulting from substitution of one hydrogen atom of the phenyl group with a trialkylstannyl group, more preferably a trialkylstannyl phenyl group resulting from substitution of a hydrogen atom at position 2, 3, or 4 of the phenyl group with a trialkylstannyl group, and furthermore preferably a substituent (4-trialkylstannyl phenyl group) resulting from substitution of a hydrogen atom at position 4 of the phenyl group with a trialkylstannyl group.

In the present invention, the "trialkylsilyl phenyl group" can be any substituent resulting from substitution of at least one hydrogen atom of the phenyl group with a trialkylsilyl group, and is preferably a substituted phenyl group resulting from substitution of one hydrogen atom of the phenyl group with a trialkylsilyl group, more preferably a trialkylsilyl phenyl group resulting from substitution of a hydrogen atom at position 2, 3, or 4 of the phenyl group with a trialkylsilyl group, and furthermore preferably a substituent (4-trialkylsilyl phenyl group) resulting from substitution of a hydrogen atom at position 4 of the phenyl group with a trialkylsilyl group.

The compound represented by the general formula (2) may form a salt. The same as the salt that may be formed by the radioactive iodine-labeled compound represented by the general formula (1) can be adopted as the salt.

The compound represented by the general formula (2) can be prepared according to, for example, the schemes shown in FIGS. 1 to 4.

The radioactive iodination reaction can be carried out by allowing a radioactive alkali metal iodide to act on the compound represented by the general formula (2) or the salt thereof. The radioactive alkali metal iodide can be any salt of radioactive iodine and an alkali metal. Examples thereof include radioactive sodium iodide and radioactive potassium iodide.

The reaction of the compound represented by the general formula (2) with the radioactive alkali metal iodide is performed under an acidic condition and further performed by reaction with an oxidizing agent. Chloramine-T, hydrogen peroxide, peracetic acid, or the like is used as the oxidizing agent.

In the case of using the obtained radioactive iodine-labeled compound of the general formula (1) as a radiopharmaceutical, it is desirable to remove unreacted radioactive iodide ions and insoluble impurities by purification using a membrane filter, a column packed with various packing materials, HPLC, or the like.

The radiopharmaceutical according to the present invention can be defined as a formulation comprising the radioactive iodine-labeled compound represented by the general formula (1) or the salt thereof in a form suitable for administration into a living body. This radiopharmaceutical can be prepared as a liquid in which the obtained radioactive iodine-labeled compound of the general formula (1) is mixed with water or saline adjusted, if desired, to appropriate pH, or a Ringer's solution or the like. In this case, it is preferred that the concentration of the present radioactive iodine-labeled compound should be equal to or lower than a concentration at which the stability of the present radioactive iodine-labeled compound mixed therein is obtained. The dosage form of the radiopharmaceutical according to the present invention is preferably an injection. The dose does not have to be particularly limited as long as it is a concentration sufficient for imaging the distribution of the administered compound.

The distribution of the present radioactive iodine-labeled compound administered into a living body can be imaged by a method known in the art and can be imaged using, for example, single photon emission computed tomography (SPECT) in the case of a [$^{123}$I]iodine-labeled compound. The tau protein can be imaged on the image thus obtained, and thus, for example, Alzheimer's disease can be noninvasively diagnosed.

EXAMPLES

Hereinafter, the present invention will be described further specifically with reference to Examples. However, the present invention is not intended to be limited by these contents.

Abbreviations used in the present Examples are defined as follows:—
BIP-1: 7-iodo-3-phenylbenzo[4,5]imidazo[1,2-a]pyridine
BIP-2: 3-(4-iodophenyl)benzo[4,5]imidazo[1,2-a]pyridine
BIP-3: 7-iodobenzo[4,5]imidazo[1,2-a]pyridine
BIP-4: 3-iodobenzo[4,5]imidazo[1,2-a]pyridine
[$^{125}$I]BIP-1: 7-[$^{125}$I]iodo-3-phenylbenzo[4,5]imidazo[1,2-a]pyridine
[$^{125}$I]BIP-2: 3-(4-[$^{125}$I]iodophenyl)benzo[4,5]imidazo[1,2-a]pyridine
[$^{125}$I]BIP-3: 7-[$^{125}$I]iodobenzo[4,5]imidazo[1,2-a]pyridine
[$^{125}$I]BIP-4: 3-[$^{125}$I]iodobenzo[4,5]imidazo[1,2-a]pyridine
[$^{123}$I]BIP-1: 7-[$^{123}$I]iodo-3-phenylbenzo[4,5]imidazo[1,2-a]pyridine
[$^{123}$I]BIP-2: 3-(4-[$^{123}$I]iodophenyl)benzo[4,5]imidazo[1,2-a]pyridine
[$^{123}$I]BIP-3: 7-[$^{123}$I]iodobenzo[4,5]imidazo[1,2-a]pyridine
[$^{123}$I]BIP-4: 3-[$^{123}$I]iodobenzo[4,5]imidazo[1,2-a]pyridine In the present Examples, reagents purchased from Nacalai Tesque, Inc., Tokyo Chemical Industry Co., Ltd., Wako Pure Chemical Industries, Ltd., or Sigma-Aldrich Co. LLC were used. However, [$^{125}$I]sodium iodide was purchased from MP Biomedical, Inc. or PerkinElmer Japan Co., Ltd. and used. An automatically set preparative medium pressure liquid chromatograph system manufactured by Yamazen Corp. (EPCLC-W-Prep 2XY; feeding pump (with a built-in mixer): No. 580D, detector (wavelength-fixed type): prep UV-254W, fraction collector: FR-260) was used as a preparative medium pressure liquid chromatography apparatus, which was equipped with HI-FLASH COLUMN (packing material: silica gel SiOH, pore size: 60 angstroms, particle size: 40 µm, column size: L or 2 L) and INJECT COLUMN (packing material: silica gel SiOH, pore size: 60 angstroms, particle size: 40 µm, column size: M or L). For NMR, measurement was performed with tetramethylsilane as internal standards using an NMR apparatus JNM-AL400 manufactured by JEOL Ltd. All chemical shifts were indicated by ppm on a delta scale (δ), and the fine splitting of signals was indicated using abbreviations (s: singlet, d: doublet, dd: double doublet, ddd: triple doublet, m: multiplet).

For mass spectrometry, measurement was performed using LCMS-2010EV manufactured by Shimadzu Corp. for atmospheric pressure chemical ionization mass spectrometry (APCI-MS) and using GCmate II manufactured by JEOL Ltd. for electron ionization mass spectrometry (EI-MS).

In the present Examples, "room temperature" means 25° C.

In the synthesis example of each compound, each step for the compound synthesis was repeated plural times according to need to secure an amount necessary for use as an intermediate or the like in other syntheses.

Wallac WIZARD 1470 manufactured by PerkinElmer Japan Co., Ltd. was used for measurement of radioactivity.

Example 1

Synthesis of 3-phenyl-7-(tributylstannyl)benzo[4,5]imidazo[1,2-a]pyridine (a Labeling Precursor Compound for the Radioactive Iodine-Labeled BIP-1)

A labeling precursor compound (compound 9) for the radioactive iodine-labeled BIP-1 was obtained according to the scheme shown in FIG. 1.

Synthesis of 2-bromo-4-phenylpyridine (Compound 7)

Dimethylaminoethanol (DMAE, 1.50 mL, 15.0 mmol) was dissolved in hexane (20.0 mL), and the solution was stirred under ice cooling. n-Butyllithium (2.5 mol/L solution in hexane, 12.0 mL, 30.0 mmol) was gradually added dropwise thereto under ice cooling, and the mixture was stirred for 30 minutes as it was. A solution of 4-phenylpyridine (776 mg, 5.00 mmol) in hexane (30.0 mL) was gradually added dropwise thereto under ice cooling, and the mixture was stirred for 1 hour as it was. The reaction solution was cooled to −78° C. Then, a solution of carbon tetrabromide (6.30 g, 18.0 mmol) in hexane (15.0 mL) was gradually added dropwise thereto, and the mixture was stirred for 50 minutes as it was. The reaction was terminated by the addition of purified water under ice cooling, followed by extraction with ethyl acetate (100 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (¼ (volume ratio)) as an elution solvent to obtain compound 7 in an amount of 645 mg (yield: 55.1%).

$^1$H-NMR (400 MHz, deuterated chloroform) δ 8.38 (d, J=5.2 Hz, 1H), 7.66-7.67 (m, 1H), 7.56-7.58 (m, 2H), 7.42-7.49 (m, 4H).

Synthesis of 7-bromo-3-phenylbenzo[4,5]imidazo[1,2-a]pyridine (Compound 8)

Compound 7 (645 mg, 2.75 mmol) was dissolved in xylene (30.0 mL). To the solution, 2,4-dibromoaniline (690 mg, 2.75 mmol), copper(I) iodide (105 mg, 0.550 mmol), cesium carbonate (2.67 g, 8.26 mmol), and 1,10-phenanthroline (198 mg, 1.10 mmol) were added, and the mixture was then heated to reflux for 24 hours with stirring. The reaction solution was brought back to room temperature, followed by extraction with ethyl acetate (100 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (¼ (volume ratio)) as an elution solvent to obtain compound 8 in an amount of 78.4 mg (yield: 8.80%).

$^1$H-NMR (400 MHz, deuterated chloroform) δ 8.47 (d, J=7.2 Hz, 1H), 8.08 (s, 1H), 7.88 (s, 1H), 7.77 (d, J=8.7 Hz, 1H), 7.72 (d, J=7.2 Hz, 2H), 7.45-7.55 (m, 4H), 7.19 (d, J=7.0 Hz, 1H).

Synthesis of 3-phenyl-7-(tributylstannyl)benzo[4,5]imidazo[1,2-a]pyridine (Compound 9)

Compound 8 (95.0 mg, 0.294 mmol) was dissolved in 1,4-dioxane (20.0 mL). To the solution, bis(tributyltin) (295 μL, 0.588 mmol), tetrakistriphenylphosphinepalladium (146 mg, 0.126 mmol), and triethylamine (16.0 mL) were added, and the mixture was heated to reflux for 3 hours with stirring. After the completion of reaction, the solvent was distilled off under reduced pressure. The residue was subjected to silica gel column chromatography with ethyl acetate/hexane (½ (volume ratio)) as an elution solvent to obtain compound 9 in an amount of 26.7 mg (yield: 17.0%).

$^1$H-NMR (400 MHz, deuterated chloroform) δ 8.48 (d, J=7.3 Hz, 1H), 8.08 (s, 1H), 7.87-7.89 (m, 2H), 7.72 (d, J=7.5 Hz, 2H), 7.44-7.53 (m, 4H), 7.12 (dd, J=7.2, 1.7 Hz, 1H), 0.87-1.63 (m, 27H).

Example 2

Synthesis of BIP-1 (Compound 10)

A non-radioactive compound (compound 10) of BIP-1 was obtained according to the scheme shown in FIG. 1.

Compound 9 (24.7 mg, 0.0463 mmol) obtained by the method shown in Example 1 was dissolved in chloroform (15.0 mL). To the solution, 1.00 mL of a solution of iodine in chloroform (50.0 mg/mL) was added, and the mixture was stirred at room temperature for 1.5 hours. The reaction was terminated with a saturated aqueous solution of sodium bisulfite, followed by extraction with chloroform (50.0 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (½ (volume ratio)) as an elution solvent to obtain compound 10 (BIP-1) in an amount of 10.3 mg (yield: 60.2%). Also, BIP-1 was obtained at a yield of 0.496% by 4-stage reaction from 4-phenylpyridine.

$^1$H-NMR (400 MHz, DMSO-d$_6$) δ 9.18 (d, J=7.3 Hz, 1H), 8.19-8.22 (m, 2H), 7.93-7.99 (m, 3H), 7.66 (dd, J=8.4, 1.4 Hz, 1H), 7.51-7.57 (m, 2H), 7.46-7.51 (m, 2H). HRMS (EI) m/z calcd for $C_{17}H_{11}IN_2$ (M$^+$) 369.9967, found 369.9960.

Example 3

Synthesis of 3-(4-(tributylstannyl)phenyl)benzo[4,5]imidazo[1,2-a]pyridine (a Labeling Precursor Compound for the Radioactive Iodine-Labeled BIP-2)

Figure 2:
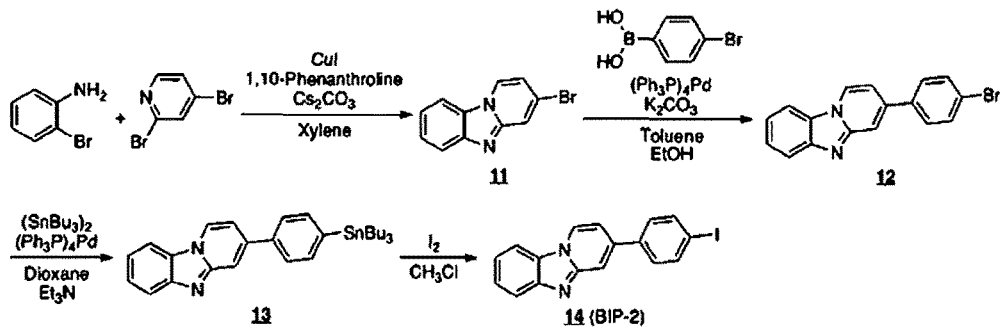
FIG. 2 is a diagram showing a synthesis example of 3-(4-iodophenyl)benzo[4,5]imidazo[1,2-a]pyridine (BIP-2) and a labeling precursor compound for the radioactive iodine-labeled BIP-2.

A labeling precursor compound (compound 13) for the radioactive iodine-labeled BIP-2 was obtained according to the scheme shown in FIG. 2.

Synthesis of 3-bromobenzo[4,5]imidazo[1,2-a]pyridine (Compound 11)

2-Bromoaniline (855 mg, 5.00 mmol) was dissolved in xylene (5.00 mL). To the solution, 2,4-dibromopyridine (1.41 g, 6.00 mmol), copper(I) iodide (191 mg, 1.00 mmol), cesium carbonate (4.89 g, 15.0 mmol), and 1,10-phenanthroline (360 mg, 2.00 mmol) were added, and the mixture was then heated to reflux for 9.5 hours with stirring. The reaction solution was brought back to room temperature, followed by extraction with ethyl acetate (100 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (¼ (volume ratio)) as an elution solvent to obtain compound 11 in an amount of 615 mg (yield: 50.0%).

$^1$H-NMR (400 MHz, deuterated chloroform) δ 8.32 (d, J=7.3 Hz, 1H), 7.94 (d, J=8.2 Hz, 1H), 7.86-7.90 (m, 2H), 7.56 (dd, J=7.3, 7.3 Hz, 1H), 7.41 (dd, J=7.3, 7.3 Hz, 1H), 6.96 (dd, J=7.1, 1.8 Hz, 1H).

Synthesis of 3-(4-bromophenyl)benzo[4,5]imidazo[1,2-a]pyridine (Compound 12)

Compound 11 (123 mg, 0.500 mmol) was dissolved in toluene (5.00 mL) and ethanol (5.00 mL). To the solution, 4-bromobenzeneboronic acid (100 mg, 0.500 mmol), tetrakistriphenylphosphinepalladium (58.0 mg, 5.00×10$^{-2}$ mmol), and potassium carbonate (14.0 mg, 0.100 mmol) were added, and the mixture was then heated to reflux for 11 hours with stirring. The reaction solution was brought back to room temperature, followed by extraction with ethyl acetate (100 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (¼ (volume ratio)) as an elution solvent to obtain compound 12 in an amount of 90.0 mg (yield: 55.9%).

$^1$H-NMR (400 MHz, DMSO-d$_6$) δ 9.18 (d, J=7.1 Hz, 1H), 8.35 (d, J=8.0 Hz, 1H), 8.02 (s, 1H), 7.91 (d, J=7.6 Hz, 2H), 7.82 (d, J=8.5 Hz, 1H), 7.74 (d, J=7.3 Hz, 2H), 7.52 (dd, J=7.3, 7.3 Hz, 1H), 7.37-7.42 (m, 2H).

Synthesis of 3-(4-(tributylstannyl)phenyl)benzo[4,5]imidazo[1,2-a]pyridine (Compound 13)

Compound 12 (90.0 mg, 0.280 mmol) was dissolved in 1,4-dioxane (5.00 mL). To the solution, bis(tributyltin) (280 μL, 0.560 mmol), tetrakistriphenylphosphinepalladium (139 mg, 0.120 mmol), and triethylamine (5.00 mL) were added, and the mixture was heated to reflux for 5 hours with stirring. After the completion of reaction, the solvent was distilled off under reduced pressure. The residue was subjected to silica gel column chromatography with ethyl acetate/hexane (¼ (volume ratio)) as an elution solvent to obtain compound 13 in an amount of 70.0 mg (yield: 47.0%).

$^1$H-NMR (400 MHz, deuterated chloroform) δ 8.46 (d, J=7.1 Hz, 1H), 7.87-7.95 (m, 3H), 7.50-7.68 (m, 5H), 7.36 (dd, J=8.0, 8.0 Hz, 1H), 7.14 (dd, J=7.1, 1.1 Hz, 1H).

Example 4

Synthesis of BIP-2 (Compound 14)

A non-radioactive compound of BIP-2 (compound 14) was obtained according to the scheme shown in FIG. 2.

Compound 13 (70.0 mg, 0.130 mmol) obtained by the method shown in Example 3 was dissolved in chloroform (30.0 mL). To the solution, 5.00 mL of a solution of iodine in chloroform (50.0 mg/mL) was added, and the mixture was stirred at room temperature for 1 hour. The reaction was terminated with a saturated aqueous solution of sodium bisulfite, followed by extraction with chloroform (100 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (¼ (volume ratio)) as an elution solvent to obtain compound 14 (BIP-2) in an amount of 10.0 mg (yield: 20.6%). Also, compound BIP-2 was obtained at a yield of 2.71% by 4-step reaction from 2-bromoaniline.

$^1$H-NMR (400 MHz, DMSO-d$_6$) δ 9.60 (d, J=7.1 Hz, 1H), 8.63 (d, J=8.5 Hz, 1H), 8.33 (s, 1H), 8.00-8.04 (m, 3H), 7.95 (d, J=8.2 Hz, 1H), 7.86 (d, J=8.7 Hz, 2H), 7.80 (dd, J=7.1, 7.1 Hz, 1H), 7.68 (dd, J=7.3, 7.3 Hz, 1H). HRMS (EI) m/z calcd for $C_{17}H_{11}IN_2$ (M$^+$) 369.9967, found 369.9970.

Example 5

Synthesis of 7-(tributylstannyl)benzo[4,5]imidazo[1,2-a]pyridine (a Labeling Precursor Compound for the Radioactive Iodine-Labeled BIP-3)

Figure 3:
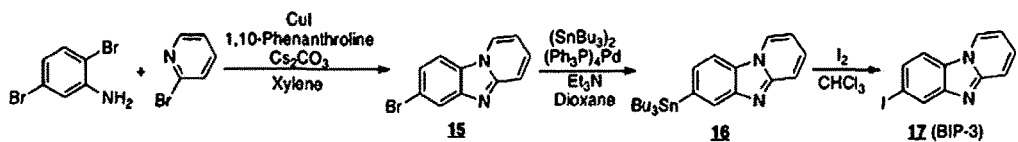
FIG. 3 is a diagram showing a synthesis example of 7-iodobenzo[4,5]imidazo[1,2-a]pyridine (BIP-3) and a labeling precursor compound for the radioactive iodine-labeled BIP-3.

A labeling precursor compound (compound 16) for the radioactive iodine-labeled BIP-3 was obtained according to the scheme shown in FIG. 3.

Synthesis of 7-bromobenzo[4,5]imidazo[1,2-a]pyridine (Compound 15)

2,5-Dibromoaniline (1.24 g, 5.00 mmol) was dissolved in xylene (5.00 mL). To the solution, 2-bromopyridine (585 μL, 6.00 mmol), copper(I) iodide (190 mg, 1.00 mmol), cesium carbonate (4.89 g, 15.0 mmol), and 1,10-phenanthroline (360 mg, 2.00 mmol) were added, and the mixture was then heated to reflux for 22 hours with stirring. The reaction solution was brought back to room temperature, followed by extraction with ethyl acetate (100 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (1/1 (volume ratio)) as an elution solvent to obtain compound 15 in an amount of 834 mg (yield: 67.8%).

$^1$H-NMR (400 MHz, deuterated chloroform) δ 9.12 (d, J=6.7 Hz, 1H), 8.31 (d, J=8.4 Hz, 1H), 8.01 (d, J=1.5 Hz, 1H), 7.69 (d, J=9.3 Hz, 1H), 7.60-7.64 (m, 1H), 7.52 (dd, J=8.7, 1.7 Hz, 1H), 7.06 (dd, J=6.7, 6.7 Hz, 1H).

Synthesis of 7-(tributylstannyl)benzo[4,5]imidazo[1,2-a]pyridine (Compound 16)

Compound 15 (834 mg, 3.39 mmol) was dissolved in 1,4-dioxane (10.0 mL). To the solution, bis(tributyltin) (3.40 mL, 6.78 mmol), tetrakistriphenylphosphinepalladium (1.69 g, 1.46 mmol), and triethylamine (10.0 mL) were added, and the mixture was heated to reflux for 6 hours with stirring. After the completion of reaction, the solvent was distilled off under reduced pressure. The residue was subjected to silica gel column chromatography with ethyl acetate/hexane (¼ (volume ratio)) as an elution solvent to obtain compound 16 in an amount of 510 mg (yield: 32.8%).

$^1$H-NMR (400 MHz, deuterated chloroform) δ 8.46 (d, J=7.0 Hz, 1H), 8.08 (s, 1H), 7.88 (d, J=8.1 Hz, 1H), 7.69 (d, J=9.3 Hz, 1H), 7.45 (d, J=8.1 Hz, 1H), 7.40-7.42 (m, 1H), 6.84 (dd, J=7.0, 7.0 Hz, 1H), 0.87-1.64 (m, 27H).

Example 6

Synthesis of BIP-3 (Compound 17)

A non-radioactive compound (compound 17) of BIP-3 was obtained according to the scheme shown in FIG. 3.

Compound 16 (510 mg, 1.11 mmol) obtained by the method shown in Example 5 was dissolved in chloroform (100 mL). To the solution, 10.0 mL of a solution of iodine in chloroform (50.0 mg/mL) was added, and the mixture was stirred at room temperature for 11 hours. The reaction was terminated with a saturated aqueous solution of sodium bisulfite, followed by extraction with chloroform (100 mL×2). The organic layer was washed with saturated saline and then dehydrated over anhydrous magnesium sulfate, and the solvent was distilled off under reduced pressure. The residue was subjected to silica gel column chromatography with ethyl acetate/hexane (1/1 (volume ratio)) as an elution solvent to obtain compound 17 (BIP-3) in an amount of 210 mg (yield: 64.2%). Also, BIP-3 was obtained at a yield of 14.3% by 3-step reaction from 2,5-dibromoaniline.

$^1$H-NMR (400 MHz, DMSO-d$_6$) δ 9.10 (dd, J=6.7, 0.9 Hz, 1H), 8.17-8.19 (m, 2H), 7.59-7.70 (m, 3H), 7.05 (dd, J=6.7, 6.7 Hz, 1H).

HRMS (EI) m/z calcd for $C_{11}H_7IN_2$(M$^+$) 293.9654, found 293.9660.

Example 7

Synthesis of 3-(tributylstannyl)benzo[4,5]imidazo[1,2-a]pyridine (a Labeling Precursor Compound for the Radioactive Iodine-Labeled BIP-4)

Figure 4:
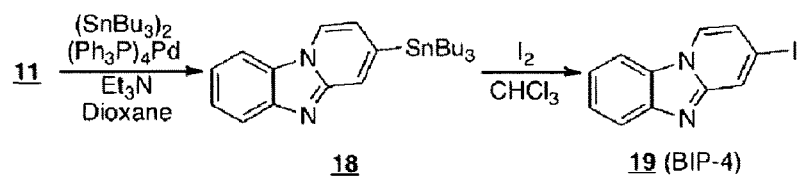
FIG. 4 is a diagram showing a synthesis example of 3-iodobenzo[4,5]imidazo[1,2-a]pyridine (BIP-4) and a labeling precursor compound for the radioactive iodine-labeled BIP-4.
Figure 5A:
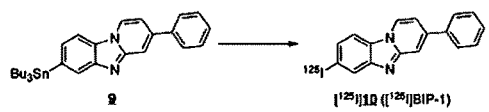
FIGS. 5A-5D are diagrams showing a labeling example of radioactive iodine-labeled pyrido[1,2-a]benzimidazole derivative compounds.
Figure 5B:
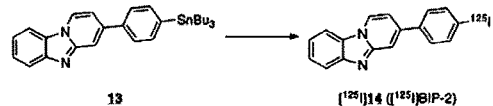
Figure 5C:
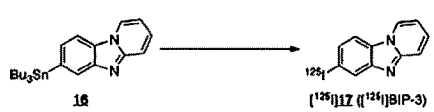
Figure 5D:
Figure 6E:
FIGS. 6E-6L are diagrams showing results of in vitro autoradiography using an autopsied brain tissue of an Alzheimer's disease patient.
Figure 6F:
Figure 6G:
Figure 6H:
Figure 6I:
Figure 6J:
Figure 6K:
Figure 6L:

A labeling precursor compound (compound 18) for the radioactive iodine-labeled BIP-4 was obtained according to the scheme shown in FIG. 4.

Compound 11 (182 mg, 0.740 mmol) obtained by the method shown in Example 3 was dissolved in 1,4-dioxane (10.0 mL). To the solution, bis(tributyltin) (741 ILL, 1.48 mmol), tetrakistriphenylphosphinepalladium (368 mg, 0.320 mmol), and triethylamine (10.0 mL) were added, and the mixture was heated to reflux for 19.5 hours with stirring. After the completion of reaction, the solvent was distilled off under reduced pressure. The residue was subjected to silica gel column chromatography with ethyl acetate/hexane (¼ (volume ratio)) as an elution solvent to obtain compound 18 in an amount of 140 mg (yield: 41.3%).

$^1$H-NMR (400 MHz, deuterated chloroform) δ 8.29 (d, J=6.6 Hz, 1H), 7.76-7.86 m, 3H), 7.44 (dd, J=8.2, 8.2 Hz, 1H), 7.26 (dd, J=8.0, 8.0 Hz, 1H), 6.82 (d, J=6.6 Hz, 1H), 0.79-1.60 (m, 27H).

Example 8

Synthesis of BIP-4 (Compound 19)

A non-radioactive compound (compound 19) of BIP-4 was obtained according to the scheme shown in FIG. 4.

Compound 18 (140 mg, 0.310 mmol) obtained by the method shown in Example 7 was dissolved in chloroform (30.0 mL). To the solution, 5.00 mL of a solution of iodine in chloroform (50.0 mg/mL) was added, and the mixture was stirred at room temperature for 1.5 hours. The reaction was terminated with a saturated aqueous solution of sodium bisulfite, followed by extraction with chloroform (100-mL× 2). The organic layer was washed with saturated saline and then dehydrated over anhydrous magnesium sulfate, and the solvent was distilled off under reduced pressure. The residue was subjected to silica gel column chromatography with ethyl acetate/hexane (¼ (volume ratio)) as an elution solvent to obtain compound 19 in an amount of 50.0 mg (yield: 55.7%). Also, BIP-4 was obtained at a yield of 11.5% by 3-step reaction from 2-bromoaniline.

$^1$H-NMR (400 MHz, DMSO-$d_6$) δ 8.91 (d, J=7.3 Hz, 1H), 8.31 (d, J=8.2 Hz, 1H), 8.18 (s, 1H), 7.81 (d, J=8.2 Hz, 1H), 7.53 (ddd, J=7.1, 7.1, 0.9 Hz, 1H), 7.39 (ddd, J=8.2, 8.2, 0.9, 1H), 7.28 (dd, J=7.1, 1.6 Hz, 1H). HRMS (EI) m/z calcd for $C_{11}H_7IN_2(M^+)$ 293.9654, found 293.9652.

Example 9

Synthesis of [$^{125}$I]BIP-1 to -4

[$^{125}$I]BIP-1 to -4 were obtained according to the scheme shown in FIG. 5. Specifically, [$^{125}$I]sodium iodide (3.7 to 7.4 MBq, specific radioactivity: 81.4 TBq/mmol) to which 1 mol/L hydrochloric acid (100 μL) and 3% (v/v) aqueous hydrogen peroxide solution (100 μL) had been added was supplemented with a solution in ethanol of compound 9 obtained by the method shown in Example 1, compound 16 obtained by the method shown in Example 5, or compound 18 obtained by the method shown in Example 7, or a solution of compound 13 obtained by the method shown in Example 3 in methanol containing 0.1% (v/v) acetic acid (1.00 mg/mL, 200 μL). After reaction at room temperature for 40 minutes, the reaction was terminated by addition of a saturated aqueous solution of sodium bisulfite (200 μL) as a reducing agent. The reaction solution was neutralized by addition of a saturated aqueous solution of sodium bicarbonate (200 μL), followed by extraction with ethyl acetate. The extract was dehydrated through a column packed with anhydrous sodium sulfate, and the solvent was then distilled off. The residue was purified using reverse phase high performance liquid chromatography (HPLC) with the corresponding non-radioactive compounds BIP-1 to -4 obtained by the methods shown in Examples 2, 4, 6, and 8 as standards, followed by extraction with ethyl acetate. LC-20AD manufactured by Shimadzu Corp. was used for HPLC, and an ultraviolet spectrum detector SPD-20A and a scintillation survey meter TCS-172 manufactured by Hitachi Aloka Medical, Ltd. were used as detectors. COSMOSIL 5$C_{18}$-AR-II manufactured by Nacalai Tesque, Inc. (4.6 mm I.D.×150 mm) was used as a column for HPLC. A mobile phase and retention time of reverse phase HPLC are shown in Table 1. The purified product was dehydrated through a column packed with anhydrous sodium sulfate, and the solvent was then distilled off. Each compound of [$^{125}$I]BIP-1 to -4 was obtained at a radiochemical yield of 45 to 85% and a radiochemical purity of 99% or higher.

TABLE 1

| Compound | Mobile phase (volume ratio) | Retention time (min) |
| --- | --- | --- |
| [$^{125}$I] BIP-1 | Acetonitrile/water = 6/4 | 13.5 |
| [$^{125}$I] BIP-2 | Acetonitrile/water = 35/65 (0.1 v/v % trifluoroacetic acid) | 6.29 |
| [$^{125}$I] BIP-3 | Acetonitrile/water = 5/5 | 8.55 |
| [$^{125}$I] BIP-4 | Acetonitrile/water = 5/5 | 7.12 |

Example 10

Synthesis of [$^{123}$I]BIP-1 to -4

[$^{123}$I]BIP-1 to -4 were obtained in the same way as in Example 9 except that 37 to 111 MBq of [$^{123}$I]sodium iodide (111 MBq/10 μL) was used instead of [$^{125}$I]sodium iodide.

(Evaluation 1) In Vitro Autoradiography Using Autopsied Brain Tissue of Alzheimer's Disease Patient (1) In Vitro Autoradiography Autopsied brain tissue sections of an Alzheimer's disease (AD) patient (76 years old, male, sections from a frontal lobe site and a temporal lobe site, 6 μm) were used, which were provided from Graduate School of Medicine, Kyoto University. Deparaffinization treatment was performed by washing with xylene (15 min×2), ethanol (1 min×2), a 90 vol % aqueous ethanol solution (1 min×1), an 80 vol % aqueous ethanol solution (1 min×1), a 70 vol % aqueous ethanol solution (1 min×1), and purified water (2.5 min×2). A 10 vol % or 50 vol % aqueous ethanol solution of each of [$^{125}$I] BIP-1 to -4 (370 kBq/mL) obtained by the method shown in Example 9 was added thereto, and the tissue sections were incubated at room temperature for 2 hours. The tissue sections were washed with a 50 vol % aqueous ethanol solution (2 hr×1), then exposed to an imaging plate (BAS-SR2025 manufactured by Fujifilm Corp.) for 12 hours, and analyzed using a bioimaging analyzer (bioimaging analyzer BAS-5000 manufactured by Fujifilm Corp.). Multi Gauge manufactured by Fujifilm Corp. was used in quantitative analysis.

The results are shown in FIG. 6. FIGS. 6E and 6F show the results obtained using [$^{125}$I]BIP-1. FIGS. 6G and 6H show the results obtained using [$^{125}$I]BIP-2. FIGS. 6I and 6J show the results obtained using [$^{125}$I]BIP-3. FIGS. 6K and 6L show the results obtained using [$^{125}$I]BIP-4. FIGS. 6E, 6G, 6I, and 6K show the results obtained using the brain tissue section of the temporal lobe. FIGS. 6F, 6H, 6J, and 6L show the results obtained using the brain tissue section of the frontal lobe. As shown in FIGS. 6F and 6H, neither [$^{125}$I]BIP-1 nor [$^{125}$I]BIP-2 exhibited radioactivity accumulation in the brain tissue section of the frontal lobe, indicating that their binding affinity for the amyloid β protein (Aβ) is low. On the other hand, as shown in FIGS. 6E and 6G, the radioactivity accumulation of [$^{125}$I]BIP-1 and [$^{125}$I]BIP-2 in the brain gray matter of the temporal lobe was maintained, indicating that they have binding affinity for tau. These compounds exhibited low nonspecific binding to the brain white matter, and, as a result, provided images with high contrast between the gray matter and the white matter. As shown in FIGS. 6I, 6J, 6K, and 6L, images equivalent to [$^{125}$I]BIP-1 and [$^{125}$I]BIP-2 were also obtained for [$^{125}$I]BIP-3 and [$^{125}$I]BIP-4.

From these results, [$^{125}$I]BIP-1 to -4 had selective binding activity for tau as compared with Aβ and further exhibited low nonspecific accumulation to the white matter, indicating the possibility that they are promising as a skeleton for a tau imaging probe.

(2) Immunostaining Using Autopsied Brain Tissue Section of AD Patient

Senile plaque (SP) and neurofibrillary tangle (NFT) were stained using sections near the brain sections used in autoradiography. An anti-Aβ$_{1-42}$ monoclonal antibody (BC05, manufactured by Wako Pure Chemical Industries, Ltd.) was used as a primary antibody in the immunostaining of SP, and an anti-phosphorylated tau monoclonal antibody (AT8, manufactured by Thermo Fisher Scientific Inc.) was used as an antibody in the immunostaining of NFT. Deparaffinization treatment was performed by washing with xylene (15 min×2), ethanol (1 min×2), a 90 vol % aqueous ethanol solution (1 min×1), an 80 vol % aqueous ethanol solution (1 min×1), a 70 vol % aqueous ethanol solution (1 min×1), and purified water (2.5 min×2). The antigens were retrieved by autoclaving (15 min) in a 0.01 mol/L citrate buffer solution (pH 6.0) and formic acid treatment (5 min). The tissue sections were washed with running water (5 min) and then washed with PBS-Tween 20 (2 min×1). The tissue sections were reacted with primary antibody solutions at room temperature for 1 hour and then washed with PBS-Tween 20 (5 min×3). The tissue sections were reacted with Histofine Simple Stain MAX-PO (MULTI) (manufactured by Nichirei Biosciences Inc.) at room temperature for 30 minutes and then washed with PBS-Tween 20 (3 min×3) and TBS (5 min×1). Finally, the tissue sections were reacted with a DAB solution at room temperature for 1 minute. The tissue sections were washed with distilled water (1 min×1) to terminate the reaction. The brain tissue sections were mounted on slides and then observed under a microscope (BZ-9000 manufactured by Keyence Corporation).

Figure 7M:
FIGS. 7M-7O are diagrams showing results of in vitro autoradiography and immunostaining using an autopsied brain tissue of an Alzheimer's disease patient.
Figure 7N:
Figure 7O:

FIG. 7M shows the results of immunostaining with the antibody against tau. FIG. 7O shows the results of immunostaining with the antibody against Aβ. FIG. 7N is an enlarged image of FIG. 6I. As a result of comparing the enlarged in vitro autoradiography image of the temporal lobe obtained using [$^{125}$I]BIP-3 with the immunostaining images of tau and Aβ, the radioactivity accumulation of [$^{125}$I]BIP-3 onto the brain tissue section of the temporal lobe (FIG. 7N) was consistent with the accumulation of tau (FIG. 7M) as compared with the accumulation of Aβ (FIG. 7O), demonstrating that [$^{125}$I]BIP-3 clearly visualizes tau accumulated in the brain with AD.

Figure 8:
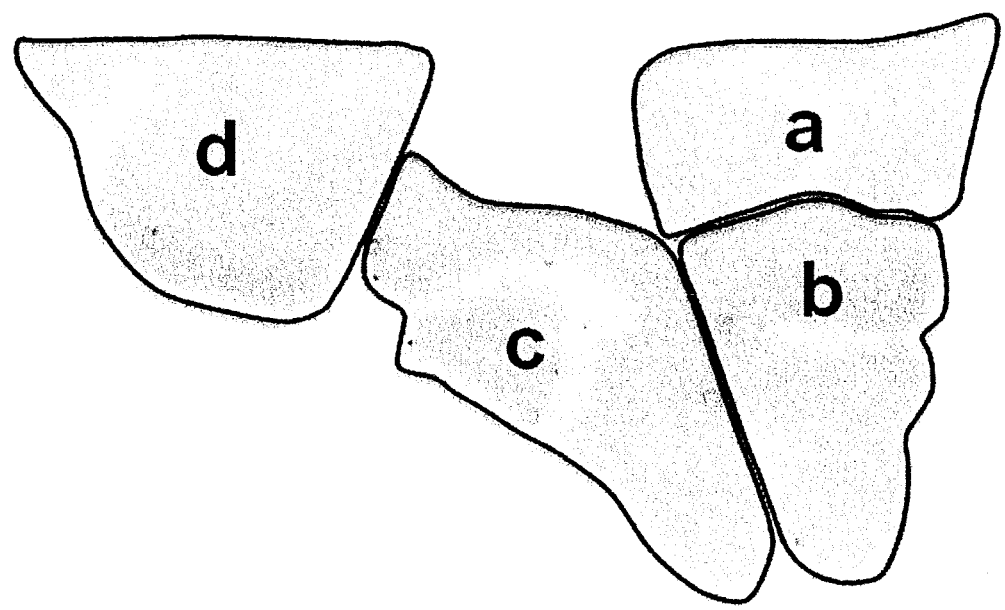
FIG. 8 is a diagram showing results of evaluating the binding affinity of [$^{125}$I]BIP-3 using a brain tissue section of the frontal lobe.
Figure 9:
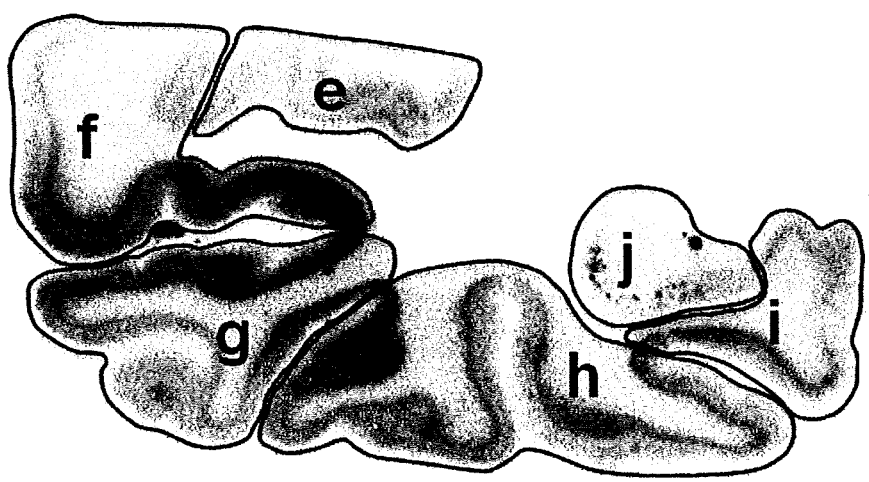
FIG. 9 is a diagram showing results of evaluating the binding affinity of [$^{125}$I]BIP-3 using a brain tissue section of the temporal lobe.
Figure 10:
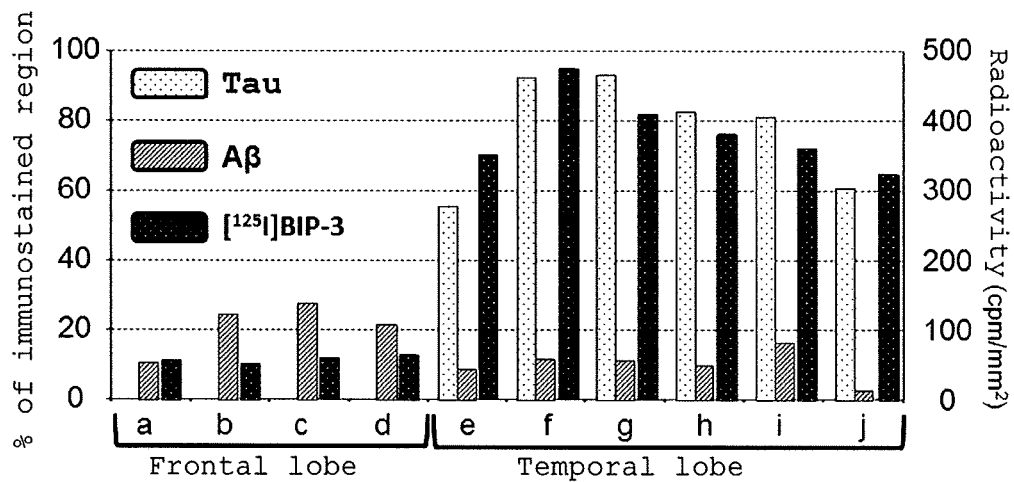
FIG. 10 is a diagram showing the proportions of immunopositive sites of tau and Aβ of each brain tissue region and the proportion of a radioactivity accumulation site of [$^{125}$I]BIP-3 relative to the whole brain tissue section, from region to region of the brain tissue.

As for [$^{125}$I]BIP-3, radioactivity accumulated on the brain tissue section was quantitatively analyzed using Multi Gauge to evaluate correlation with immunostaining positive sites of tau and Aβ. As shown in FIG. 8, the frontal lobe was classified into 4 sites: a. cingulate gyrus, b. straight gyrus, c. inferior frontal gyrus, and d. superior frontal gyrus. As shown in FIG. 9, the temporal lobe was classified into 6 sites: e. transverse temporal gyrus, f. superior temporal gyrus, g. middle temporal gyrus, h. inferior frontal gyrus, i. parahippocampal gyrus, and j. hippocampus. As a result of calculating the ratios of the immunostaining positive sites of tau and Aβ to the whole area of each site, only Aβ was quantitatively shown to accumulate in the frontal lobe (FIGS. 10a to 10d). On the other hand, the temporal lobe was shown to have a high ratio of the immunostaining positive site of tau as compared with Aβ (FIGS. 10e to 10j). As a result of comparing the ratios of the immunostaining positive sites of tau and Aβ with the radioactivity accumulation of [$^{125}$I]BIP-3, [$^{125}$I]BIP-3 exhibited low radioactivity accumulation to the frontal lobe (FIGS. 10a to 10d) and higher radioactivity accumulation to the temporal lobe than the radioactivity accumulation to the frontal lobe (FIGS. 10e to 10j), indicating that the radioactivity accumulation of [$^{125}$I]BIP-3 onto brain tissue sections correlates with the rate of accumulation of tau as compared with Aβ.

(Evaluation 2) Comparison of Intracerebral Kinetics

Each of [$^{125}$I]BIP-1 to -4 obtained by the method shown in Example 9 was diluted with saline containing 10 vol % ethanol and 0.1 vol % Tween 80. Each of [$^{125}$I]BIP-1 to -4 was administered to a group of 5-week-old ddY male mice (26 to 28 g; each group involved 5 mice) from the tail veins thereof at 25.0 to 37.5 kBq (100 μL) per mouse. After 2, 10, 30, or 60 minutes, the mice were slaughtered. After blood collection, the brains were taken out, and their weights and radioactivity were measured. As for [$^{125}$I]BIP-3, the principal organs were also excised, and their weights and radioactivity were measured.

Figure 11:
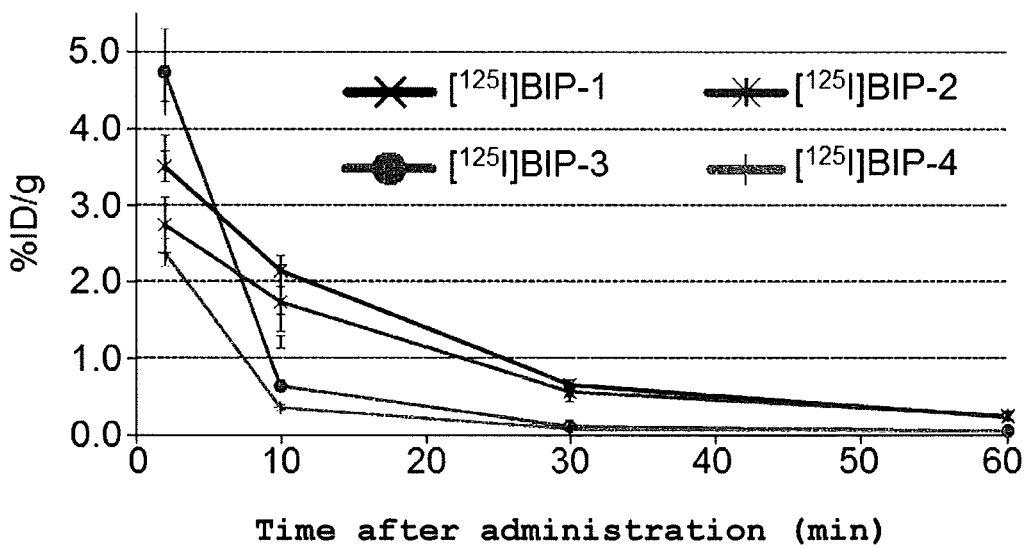
FIG. 11 is a diagram showing results of comparing the intracerebral kinetics of the radioactive iodine-labeled pyrido[1,2-a]benzimidazole derivative compounds according to Examples.

The results are shown in Table 2 and FIG. 11. In Table 2, the numerical values shown in the column "Time after administration" are means of % ID/g with standard deviation (SD) shown in parenthesis. [$^{125}$I]BIP-1 to -4 exhibited high transfer to the brain early after administration and then rapid clearance from the brain. Among others, the radioactivity (Brain$_{2min}$) of [$^{125}$I]BIP-3 in the brain 2 minutes after administration was 4.74% ID/g. The ratio (Brain$_{2min/60min}$) of radioactivity of [$^{125}$I]BIP-3 in the brain between 2 minutes and 60 minutes after administration was 79.0, indicating that it exhibits favorable intracerebral kinetics.

TABLE 2

| | Time after administration (min) | | | | |
|---|---|---|---|---|---|
| Compound | 2 | 10 | 30 | 60 | Brain$_{2 min/60 min}$ |
| [$^{125}$I] BIP-1 | 3.51 (0.20) | 2.14 (0.21) | 0.65 (0.06) | 0.23 (0.03) | 15.3 |
| [$^{125}$I] BIP-2 | 2.73 (0.37) | 1.73 (0.39) | 0.57 (0.07) | 0.26 (0.05) | 10.4 |
| [$^{125}$I] BIP-3 | 4.74 (0.57) | 0.65 (0.07) | 0.12 (0.01) | 0.06 (0.01) | 79.0 |
| [$^{125}$I] BIP-4 | 2.37 (0.18) | 0.36 (0.05) | 0.09 (0.01) | 0.06 (0.01) | 39.5 |

Results of conducting an in vivo radioactivity distribution experiment of [$^{125}$I]BIP-3 are shown in Table 3. In Table 3, the numerical values shown in the column "Time after administration" are means of % ID for the stomach and the thyroid gland and means of % ID/g for the other tissues with standard deviation (SD) shown in parenthesis. Uptake into the kidney (23.7% ID/g) and uptake into the liver (19.9% ID/g) 2 minutes after administration were at the same level. Also, uptake into the intestine 60 minutes after administration was 29.4% ID/g, indicating a behavior of being gradually excreted from the liver to the intestine. Furthermore, uptake into the thyroid gland was 0.22% ID even 60 minutes after administration, and accumulation to the thyroid gland in conjunction with deiodination was relatively low, suggesting that marked deiodination does not occur in living body.

TABLE 3

| Tissue | Time after administration (min) | | | |
|---|---|---|---|---|
| | 2 | 10 | 30 | 60 |
| Blood | 5.20 (0.44) | 2.94 (0.41) | 1.30 (0.16) | 1.11 (0.53) |
| Liver | 19.9 (1.39) | 14.4 (2.14) | 6.29 (0.45) | 5.25 (0.95) |
| Kidneys | 23.7 (2.44) | 12.2 (1.55) | 10.3 (5.11) | 8.99 (4.47) |
| Intestine | 5.41 (0.62) | 11.6 (2.43) | 21.4 (5.69) | 29.4 (7.49) |
| Spleen | 4.76 (0.39) | 1.34 (0.28) | 0.58 (0.16) | 0.71 (0.11) |
| Pancreas | 5.36 (0.91) | 1.49 (0.47) | 0.78 (0.47) | 0.75 (0.30) |
| Heart | 7.66 (1.21) | 1.66 (0.75) | 0.97 (0.26) | 0.83 (0.24) |
| Lungs | 29.7 (4.63) | 6.32 (1.16) | 1.91 (0.29) | 1.45 (0.23) |
| Stomach | 2.70 (0.56) | 6.73 (1.64) | 5.34 (1.26) | 4.42 (2.43) |
| Brain | 4.74 (0.57) | 0.65 (0.07) | 0.12 (0.01) | 0.06 (0.01) |
| Thyroid gland | 0.09 (0.03) | 0.06 (0.02) | 0.13 (0.03) | 0.22 (0.03) |

(Evaluation 3) Stability Evaluation of [$^{125}$I]BIP-3 in Plasma

Blood was collected from the heart of a ddY mouse (5 weeks old, body weight: 25 to 28 g) under anesthesia with isoflurane. The collected blood was fractionated by centrifugation at 4000×g for 10 minutes to recover a supernatant. [$^{125}$I]BIP-3 obtained by the method shown in Example 9 (188 kBq, 10.0 μL, ethanol solution) and the mouse plasma sample (200 μL) were mixed. The mixture was incubated at 37° C. for 1 hour, and acetonitrile (400 μL) was added thereto, followed by fractionation by centrifugation at 4000×g for 10 minutes. The supernatant was recovered, treated with Cosmonice Filter (S) (0.45 μm, 4 mm) (Nacalai Tesque, Inc.), and then analyzed by reverse phase HPLC. Analytical conditions for HPLC were the same as the conditions used in Example 9.

Figure 12:
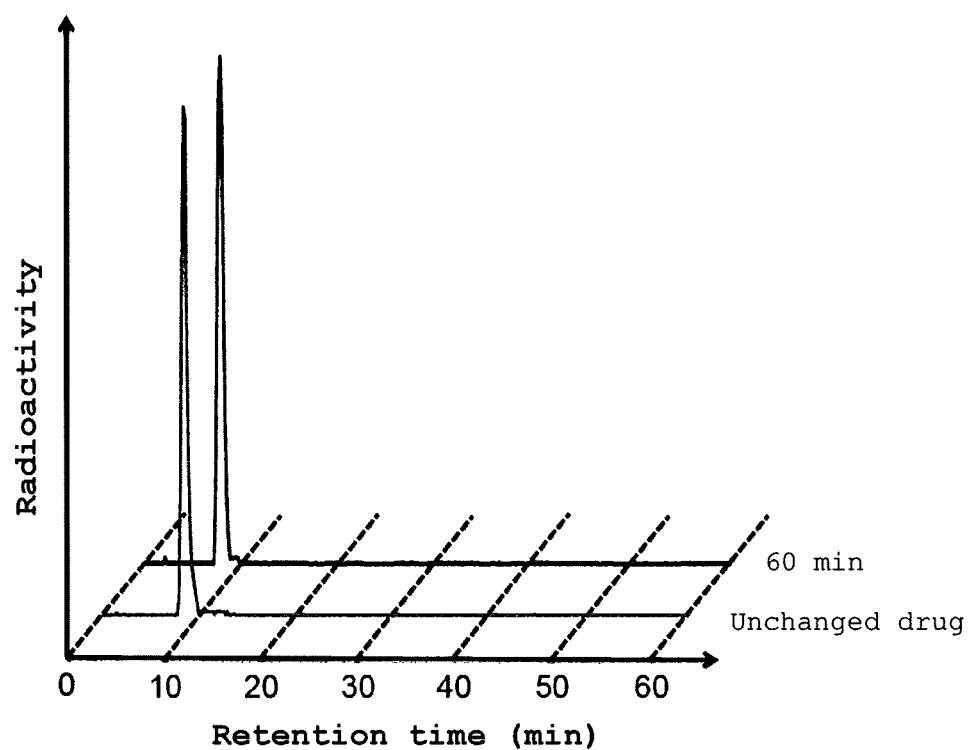
FIG. 12 is a diagram showing results of evaluating the stability of the radioactive iodine-labeled BIP-3 in plasma.

The stability of [$^{125}$I]BIP-3 in the mouse plasma was evaluated. As a result of analyzing the sample incubated in the mouse plasma for 1 hour by reverse phase HPLC, only the peak of the parent compound was detected (FIG. 12). These results indicated that [$^{125}$I]BIP-3 is stably present in mouse plasma up to 1 hour.

(Evaluation 4) Log P Value Measurement

Each of [$^{125}$I]BIP-1 to -4 (125 kBq) obtained by the method shown in Example 9 was added to a centrifuge tube containing 1-octanol (3.00 mL) and a 0.1 mol/L phosphate buffer solution (pH 7.4, 3.00 mL), vortexed for 2 minutes, and then centrifuged at 4,000×g for 10 minutes. 500 μL of a solution was collected from each layer, and the radioactivity thereof was then measured. A partition coefficient was determined from the 1-octanol/phosphate buffer solution ratio of radioactivity. The results are shown in Table 4.

TABLE 4

| Compound | Log P |
|---|---|
| [$^{125}$I] BIP-1 | 2.64 |
| [$^{125}$I] BIP-2 | 2.61 |
| [$^{125}$I] BIP-3 | 3.22 |
| [$^{125}$I] BIP-4 | 2.35 |

(Evaluation 5) Metabolite Analysis of [$^{123}$I]BIP-3 in Blood.

A 5-week-old male ddY mouse was used as a normal mouse. [$^{123}$I]BIP-3 obtained by the method shown in Example 10, which was contained in saline containing 0.1 vol % Tween 80 and 10 vol % ethanol, was administered from the tail vein (3.70 MBq, 100 μL). 2 minutes, 10 minutes, or 30 minutes after administration, the mouse was slaughtered, and blood was collected into a test tube with an inner wall coated with Heparin Sodium Injection (manufactured by Nipro Pharma Corp.). After radioactivity measurement, the blood was centrifuged at 4000×g at 4° C. for 5 minutes and separated into plasma and cell components. To the obtained plasma, a 2-fold volume of methanol was added for protein denaturation, and the mixture was centrifuged at 4000×g at 4° C. for 5 minutes. The obtained supernatant was passed through Cosmonice Filter (S) (0.45 μm, 4 mm) (Nacalai Tesque, Inc.) and analyzed by reverse phase HPLC. Analytical conditions for HPLC were the same as the conditions used in Example 9.

Figure 13:
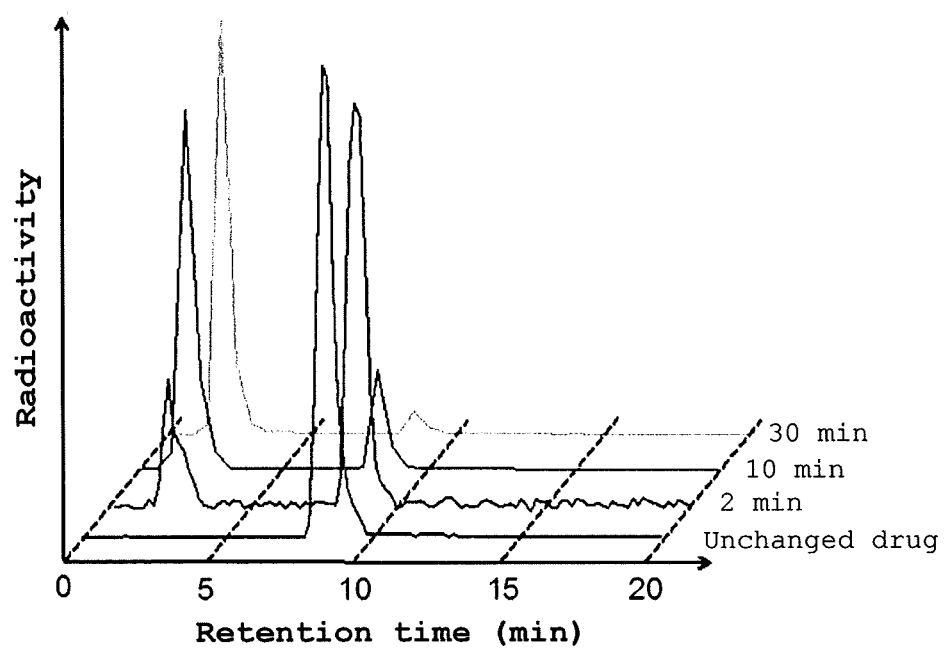
FIG. 13 is a diagram showing results of analyzing metabolites of the radioactive iodine-labeled BIP-3 in blood.

The results are shown in FIG. 13 and Table 5. In Table 5, the proportion of the parent compound is indicated by mean±standard deviation of n=3. It was suggested that [$^{123}$I]BIP-3 forms a highly water-soluble metabolite after administration to mice, as compared with the parent compound (FIG. 13). The parent compound was present in blood at a proportion shown in Table 5.

TABLE 5

| Time after administration (min) | Proportion of parent compound |
|---|---|
| 2 | 83.1 ± 7.7 |
| 10 | 23.6 ± 2.2 |
| 30 | 8.4 ± 1.1 |

(Evaluation 6) Metabolite Analysis of [$^{123}$I]BIP-3 in Brain

A 5-week-old male ddY mouse was used as a normal mouse. [$^{123}$I]BIP-3 obtained by the method shown in Example 10, which was contained in saline containing 0.1 vol % Tween 80 and 10 vol % ethanol, was administered from the tail vein (3.70 MBq, 100 ILL). After 2 minutes, the mouse was slaughtered, and the brain was excised, homogenized in methanol (2.00 mL) and TBS (2.00 mL), and centrifuged at 4000×g at 4° C. for 10 minutes, followed by the collection of a supernatant. The obtained supernatant was passed through Cosmonice Filter (S) (0.45 μm, 4 mm) (Nacalai Tesque, Inc.) and analyzed by reverse phase HPLC. Analytical conditions for HPLC were the same as the conditions used in Example 9.

Figure 14:
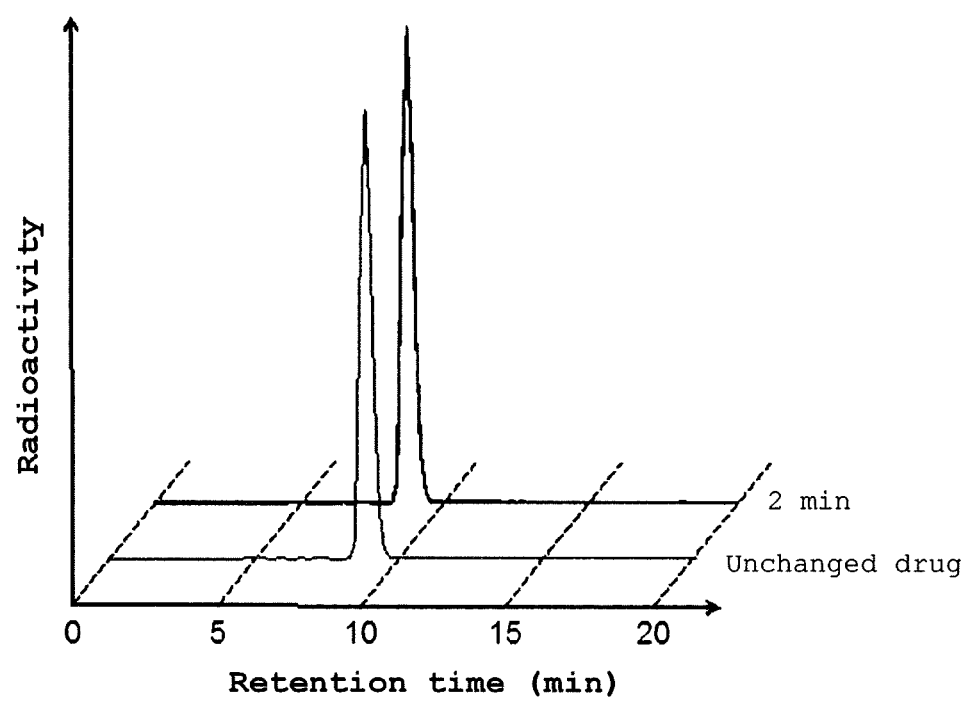
FIG. 14 is a diagram showing results of analyzing metabolites of the radioactive iodine-labeled BIP-3 in brain.

The results are shown in FIG. 14. As a result of analyzing the brain homogenates by reverse phase HPLC, only the signal peak of the parent compound was detected, indicating that [$^{123}$I]BIP-3 is stably present in the mouse brain. It was also suggested that the metabolite detected in the blood sample is not transferred to the brain.

The results shown above indicated that the radioactive iodine-labeled compound according to the present invention can selectively and noninvasively image the tau protein in the brain.

This application claims the priority based on Japanese Patent Application No. 2015-042748 filed on Mar. 4, 2015, the disclosure of which is incorporated herein in its entirety.

The invention claimed is:

1. A radioactive iodine-labeled compound represented by the following formula (1) or a salt thereof:

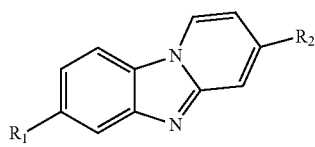

(1)

wherein when $R_1$ is a hydrogen atom, $R_2$ is a radioactive iodine atom or a radioactive iodophenyl group, and when $R_1$ is a radioactive iodine atom, $R_2$ is a hydrogen atom or a phenyl group.

2. The radioactive iodine-labeled compound or a salt thereof according to claim 1, wherein the radioactive iodophenyl group is a substituent having a phenyl group which hydrogen atom at position 4 is substituted with a radioactive iodine atom.

3. The radioactive iodine-labeled compound or a salt thereof according to claim 1, wherein the radioactive iodine atom is $^{123}I$, $^{124}I$, $^{125}I$, or $^{131}I$.

4. A radiopharmaceutical comprising a radioactive iodine-labeled compound or a salt thereof according to claim 1.

5. The radiopharmaceutical according to claim 4, which is for use in single photon emission computed tomography (SPECT).

6. A diagnostic agent for Alzheimer's disease comprising a radioactive iodine-labeled compound or a salt thereof according to claim 1.

7. A compound represented by the following formula (2) or a salt thereof:

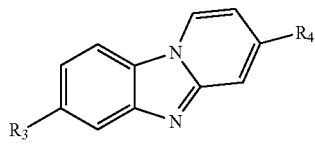

(2)

wherein when $R_3$ is a hydrogen atom, $R_4$ is a trialkylstannyl group, a trialkylsilyl group, a trialkylstannyl phenyl group, or a trialkylsilyl phenyl group, and when $R_3$ is a trialkylstannyl group or a trialkylsilyl group, $R_4$ is a hydrogen atom or a phenyl group.

8. A method for producing a radioactive iodine-labeled compound, comprising the step of sublectinq a compound represented by the following formula (2) or a salt thereof to a radioactive iodination reaction to obtain a radioactive iodine-labeled compound represented by the following formula (1):

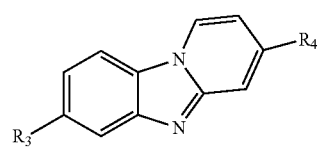

(2)

wherein when $R_3$ is a hydrogen atom, $R_4$ is a trialkylstannyl group, a trialkylsilyl group, a trialkylstannyl phenyl group, or a trialkylsilyl phenyl group, and when $R_3$ is a trialkylstannyl group or a trialkylsilyl group, $R_4$ is a hydrogen atom or a phenyl group, and

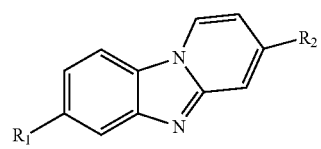

(1)

wherein when $R_1$ is a hydrogen atom, $R_2$ is a radioactive iodine atom or a radioactive iodophenyl group, and when $R_1$ is a radioactive iodine atom, $R_2$ is a hydrogen atom or a phenyl group.

* * * * *